(12) United States Patent
Brierton et al.

(10) Patent No.: US 11,071,599 B2
(45) Date of Patent: Jul. 27, 2021

(54) SURGICAL INSTRUMENT ENGAGEMENT DETECTION

(71) Applicant: CMR Surgical Limited, Cambridge (GB)

(72) Inventors: Ben Brierton, Cambridge (GB); Andrew Murray Scholan, Newmarket (GB); Simon Schofield, Cambridge (GB); Ricardo Michael Henderson Da Silva, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 398 days.

(21) Appl. No.: 15/880,641

(22) Filed: Jan. 26, 2018

(65) Prior Publication Data

US 2018/0228559 A1   Aug. 16, 2018

(30) Foreign Application Priority Data

Jan. 31, 2017   (GB) ...................................... 1701525

(51) Int. Cl.
| | |
|---|---|
| *A61B 34/30* | (2016.01) |
| *A61B 90/90* | (2016.01) |
| *A61B 90/98* | (2016.01) |
| *A61B 46/10* | (2016.01) |
| *A61B 34/37* | (2016.01) |

(Continued)

(52) U.S. Cl.
CPC .............. *A61B 34/30* (2016.02); *A61B 34/37* (2016.02); *A61B 46/10* (2016.02); *A61B 90/90* (2016.02); *A61B 90/98* (2016.02); *A61B 34/20* (2016.02); *A61B 2017/00199* (2013.01); *A61B 2017/00221* (2013.01); *A61B 2017/00477* (2013.01); *A61B 2017/00482* (2013.01); *A61B 2034/302* (2016.02); *A61B 2034/305* (2016.02); *A61B 2034/742* (2016.02); *A61B 2090/064* (2016.02);

(Continued)

(58) Field of Classification Search
CPC combination set(s) only.
See application file for complete search history.

(56) References Cited

U.S. PATENT DOCUMENTS

| | | | |
|---|---|---|---|
| 6,645,196 B1 * | 11/2003 | Nixon | B25J 9/1664 |
| | | | 128/898 |
| 8,157,795 B2 * | 4/2012 | Sartor | A61B 18/042 |
| | | | 606/41 |

(Continued)

FOREIGN PATENT DOCUMENTS

| | | |
|---|---|---|
| EP | 1815950 | 8/2007 |
| KR | 20090081094 | 7/2009 |

(Continued)

*Primary Examiner* — Bhavesh V Amin
(74) *Attorney, Agent, or Firm* — r Occhiuti & Rohlicek LLP

(57) ABSTRACT

A surgical robot comprising a robot arm base connected to a distal robot arm link via a series of intermediate articulated robot arm links. A robot arm interface is attached to the distal robot arm link. The robot arm interface engages an instrument interface of a surgical instrument, and comprises an instrument engagement source and an instrument engagement detector. The instrument engagement detector is configured to only detect the instrument engagement source when the instrument engagement source is coupled to the instrument engagement detector by a coupler.

20 Claims, 9 Drawing Sheets

(51) Int. Cl.
*A61B 90/00* (2016.01)
*A61B 17/00* (2006.01)
*A61B 34/00* (2016.01)
*A61B 34/20* (2016.01)

(52) U.S. Cl.
CPC ............... *A61B 2090/0803* (2016.02); *A61B 2090/0808* (2016.02)

(56) References Cited

U.S. PATENT DOCUMENTS

| | | | |
|---|---|---|---|
| 8,463,439 B2 * | 6/2013 | Blumenkranz | G01B 11/16 |
| | | | 700/258 |
| 10,420,617 B2 * | 9/2019 | Scholan | B25J 3/04 |
| 2006/0161138 A1 * | 7/2006 | Orban, III | A61B 34/35 |
| | | | 606/1 |
| 2008/0147089 A1 | 6/2008 | Loh et al. | |
| 2009/0206130 A1 * | 8/2009 | Hall | A61B 17/07207 |
| | | | 227/175.2 |
| 2010/0036384 A1 * | 2/2010 | Gorek | A61B 90/39 |
| | | | 606/104 |
| 2010/0250000 A1 * | 9/2010 | Blumenkranz | A61B 34/20 |
| | | | 700/258 |
| 2011/0288573 A1 * | 11/2011 | Yates | A61B 17/07207 |
| | | | 606/170 |
| 2012/0190981 A1 * | 7/2012 | Harris | A61B 5/150389 |
| | | | 600/439 |
| 2012/0286019 A1 * | 11/2012 | Hueil | A61B 17/068 |
| | | | 227/175.1 |
| 2013/0116706 A1 * | 5/2013 | Lee | A61B 34/30 |
| | | | 606/130 |
| 2013/0331650 A1 * | 12/2013 | Blumenkranz | A61B 34/30 |
| | | | 600/130 |
| 2014/0128886 A1 * | 5/2014 | Holop | A61B 18/14 |
| | | | 606/130 |
| 2014/0195052 A1 * | 7/2014 | Tsusaka | A61B 34/76 |
| | | | 700/257 |
| 2014/0276950 A1 * | 9/2014 | Smaby | A61B 90/361 |
| | | | 606/130 |
| 2015/0216515 A1 * | 8/2015 | Newell | A61B 17/1622 |
| | | | 606/1 |
| 2015/0352715 A1 * | 12/2015 | Yanagihara | B25J 9/06 |
| | | | 74/89.23 |
| 2016/0151115 A1 | 6/2016 | Karguth et al. | |
| 2016/0151120 A1 * | 6/2016 | Kostrzewski | A61B 90/50 |
| | | | 606/130 |
| 2016/0202134 A1 * | 7/2016 | Malackowski | B25J 9/1694 |
| | | | 73/862.05 |
| 2016/0310221 A1 * | 10/2016 | Bar | A61B 34/20 |
| 2017/0042730 A1 * | 2/2017 | He | G09B 19/24 |
| 2017/0173262 A1 * | 6/2017 | Veltz | A61B 5/0022 |
| 2018/0228559 A1 * | 8/2018 | Brierton | A61B 34/37 |

FOREIGN PATENT DOCUMENTS

| | | |
|---|---|---|
| WO | 20110037394 | 3/2011 |
| WO | 2015132549 | 9/2015 |

* cited by examiner

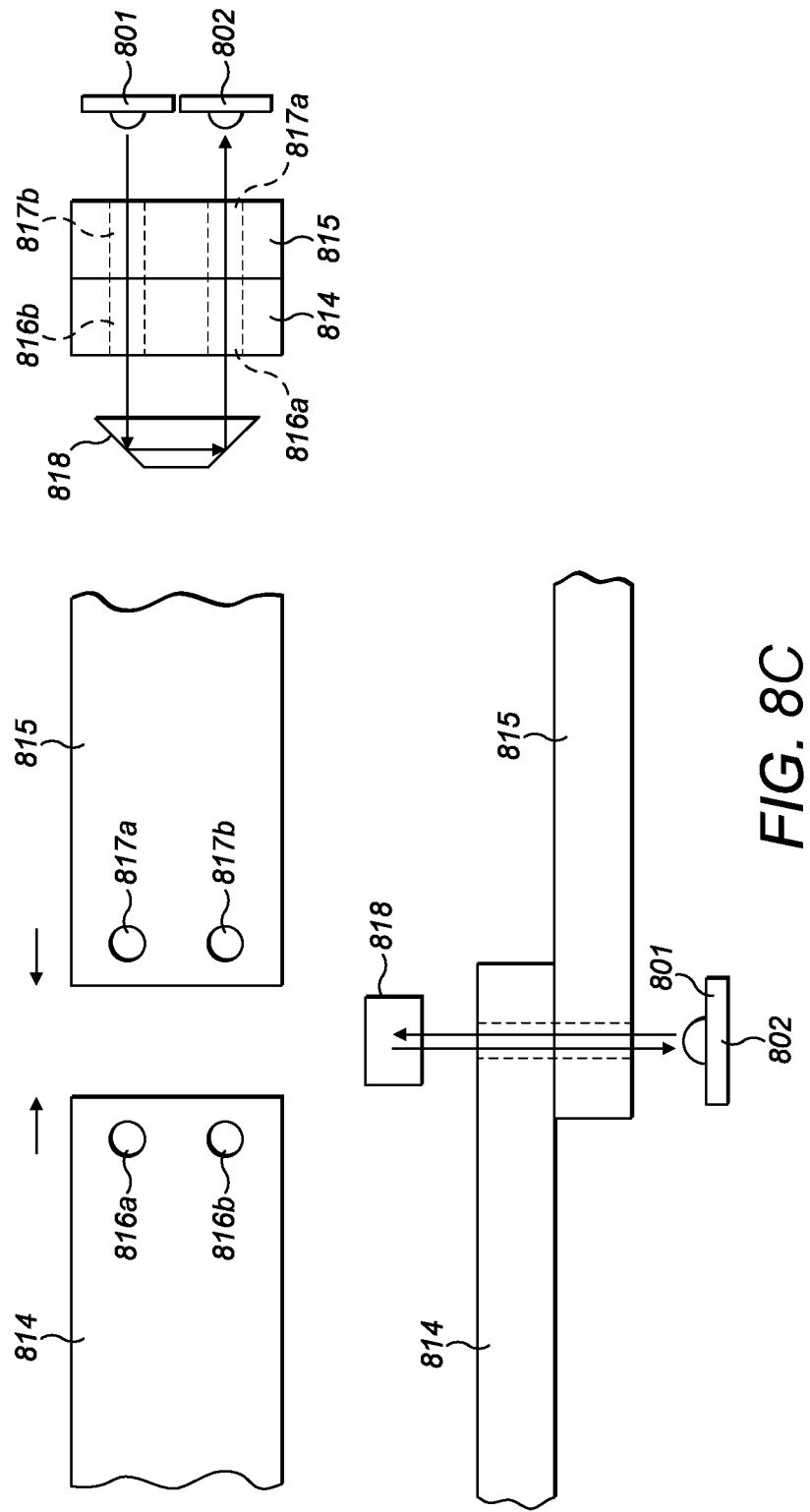

SURGICAL INSTRUMENT ENGAGEMENT DETECTION

CROSS REFERENCE TO RELATED APPLICATIONS

This application claims priority to Great Britain Application No. 1701525.6 filed on Jan. 31, 2017, the contents of which are hereby incorporated by reference in their entirety.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

A surgeon utilises many instruments during the course of a typical laparoscopy operation. For this reason, surgical robots typically have instruments which are detachable from and attachable to the end of the robot arm mid-operation. It is desirable for there to be a mechanism which detects that the instrument has been attached to the robot arm before the instrument is used for manipulation at the surgical site.

It is known to integrate a magnet on the instrument and to integrate a sensor on the robot arm for detecting the magnetic field from the magnet. The sensor detects the magnet when the instrument is attached to the robot arm. Although this approach detects that the instrument has been attached to the robot arm, it does not detect whether the instrument has been properly engaged with the robot arm. An attached but misaligned instrument would also be detected by the sensor.

Thus, there is a need for a surgical robot which is able to detect that an instrument has been attached to and properly engaged with the robot arm.

SUMMARY OF THE INVENTION

According to an aspect of the invention there is provided a surgical robot comprising: a robot arm base connected to a distal robot arm link via a series of intermediate articulated robot arm links; a robot arm interface attached to the distal robot arm link, the robot arm interface configured to engage an instrument interface of a surgical instrument, the robot arm interface comprising: an instrument engagement source; and an instrument engagement detector configured to only detect the instrument engagement source when the instrument engagement source is coupled to the instrument engagement detector by a coupler.

The instrument engagement detector may only detect the instrument engagement source via the coupler when the instrument interface and the robot arm interface are engaged.

The instrument engagement source and instrument engagement detector may be short-range and only coupleable by a coupler located proximally to both the instrument engagement source and instrument engagement detector.

The surgical robot may further comprise a controller configured to determine that an instrument interface of a surgical instrument is engaged with the robot arm interface in response to the instrument engagement detector detecting the instrument engagement source.

The controller may be configured to modify an operational mode of the surgical robot in response to the instrument engagement detector detecting the instrument engagement source.

The surgical robot may comprise a receiver configured to receive data from the surgical instrument over a short-range wireless communications link with the surgical instrument, wherein the controller is configured to respond to the instrument engagement detector detecting the instrument engagement source by enabling the short-range wireless communications link between the receiver and a transmitter of the surgical instrument to be established.

The surgical robot may comprise a transmitter configured to transmit data to the surgical instrument over the short-range wireless communications link, wherein the controller is configured to respond to the instrument engagement detector detecting the instrument engagement source by transmitting a request for data from the transmitter to the surgical instrument.

The instrument engagement source may be a magnet, and the instrument engagement detector a Hall sensor.

The magnet may be spaced apart from the Hall sensor on the robot arm interface such that the magnet is only detectable by the Hall sensor when coupled to the Hall sensor by a magnetically permeable coupler located proximal to the magnet and Hall sensor.

The instrument engagement source may be a light source, and the instrument engagement detector a light sensor.

The light from the light source may be directed away from the light sensor such that light from the light source is only detectable by the light sensor when directed onto the light sensor by a coupler which provides a light path from the light source to the light sensor.

The instrument engagement source and the instrument engagement detector may be collectively a sensor array which is configured to be activated by a metal array coupler located proximal to the sensor array.

The sensor array may comprise a plurality of sensors, and the sensor array may be configured to be activated when a predetermined pattern of the plurality of sensors is activated.

The controller may be configured to identify the surgical instrument from the activated predetermined pattern of the plurality of sensors.

The sensor array may be a capacitive sensor array. The sensor array may be an inductive sensor array.

The coupler may be external to the robot arm interface.

The surgical robot may further comprise a surgical instrument comprising an instrument interface.

The robot arm interface may comprise the coupler.

The instrument interface may comprise the coupler.

The surgical robot may further comprise a surgical drape for draping the robot arm, the drape comprising the coupler.

The coupler may be configured to connect a circuit between the instrument engagement source and the instrument engagement detector.

The instrument interface may comprise an instrument transmitter configured to transmit data over the short-range wireless communications link.

The instrument interface may comprise an instrument receiver configured to receive data requests from the robot arm interface, and the instrument transmitter may be configured to respond to a data request from the robot arm interface by transmitting the requested data to the surgical robot.

The coupler may be located on a moveable feature which is moveable relative to the robot arm interface. The instrument interface may comprise a protrusion, such that when the instrument interface and robot arm interface are engaged, the protrusion pushes the moveable feature towards the robot arm interface so as to cause the coupler to couple the instrument engagement source to the instrument engagement detector.

The coupler may be magnetically permeable.

The coupler may provide a light path from the light source to the light sensor.

The instrument interface may comprise an engagement mechanism moveable between a disengaged configuration and an engaged configuration, wherein the coupler only provides the light path from the light source to the light sensor when the instrument interface and robot arm interface are engaged and the engagement mechanism is in the engaged configuration.

The coupler may comprise a series of openings on the engagement mechanism, the openings configured to align to form the light path only when the mechanism is in the engaged configuration.

The coupler may be a metal array.

The metal array may have a pattern which matches the predetermined pattern of the plurality of sensors.

BRIEF DESCRIPTION OF THE FIGURES

The present invention will now be described by way of example with reference to the accompanying drawings. In the drawings:

FIGS. 8A, 8B, and 8C illustrate a light path example of the circuitry of FIGS. 4 and 5;

DETAILED DESCRIPTION

Figure 3:
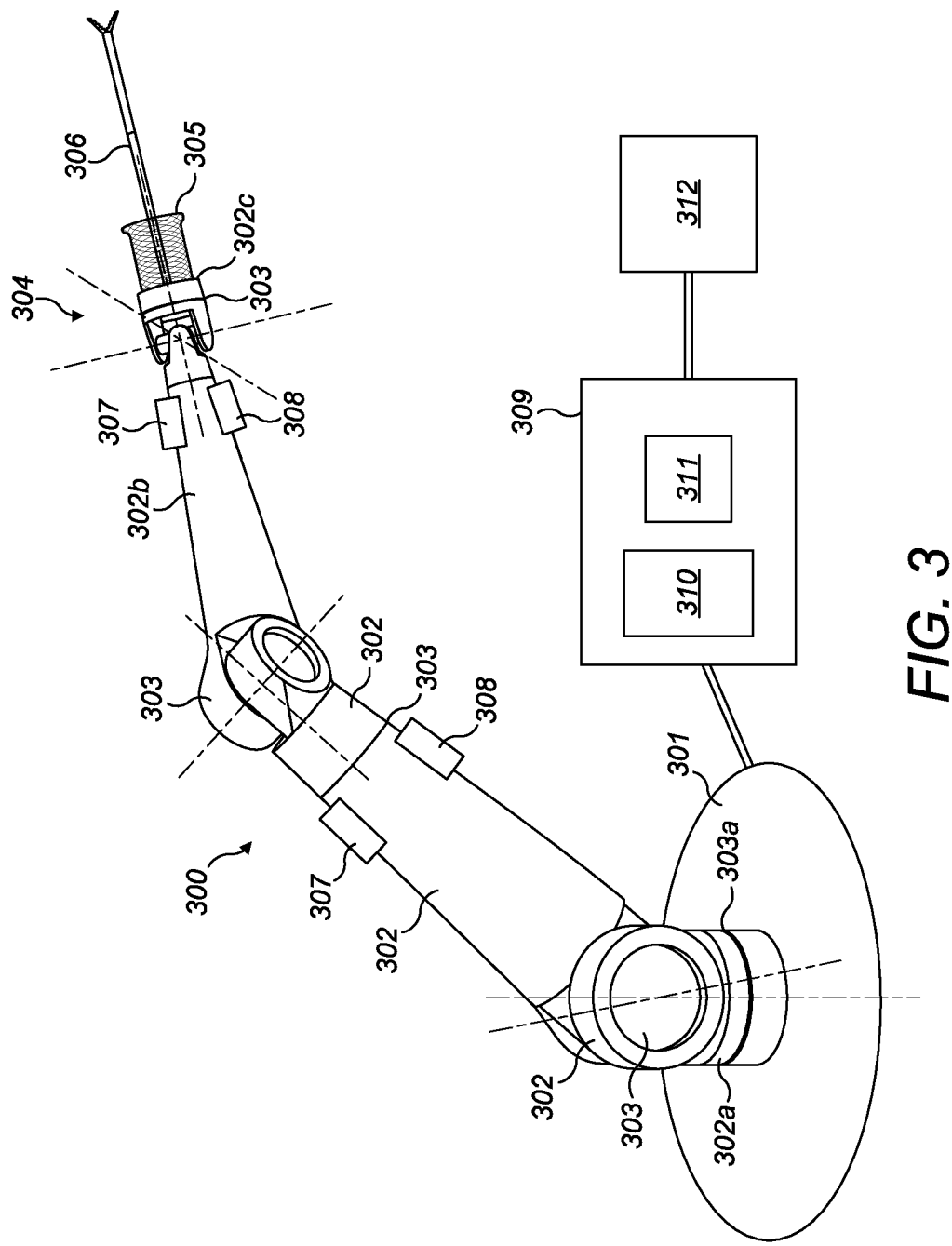
FIG. 3 illustrates a surgical robot.

FIG. 3 illustrates a surgical robot having an arm 300 which extends from a proximal end attached to a base 301. The arm comprises a number of rigid links 302. The links are coupled by revolute joints 303. The most proximal link 302a is coupled to the base by joint 303a. It and the other links are coupled in series by further ones of the joints 303. Suitably, a wrist 304 is made up of four individual revolute joints. The wrist 304 couples one link (302b) to the most distal link (302c) of the arm. The most distal link 302c is at the distal end of the arm and carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our co-pending patent application PCT/GB2014/053523.

Figure 1:
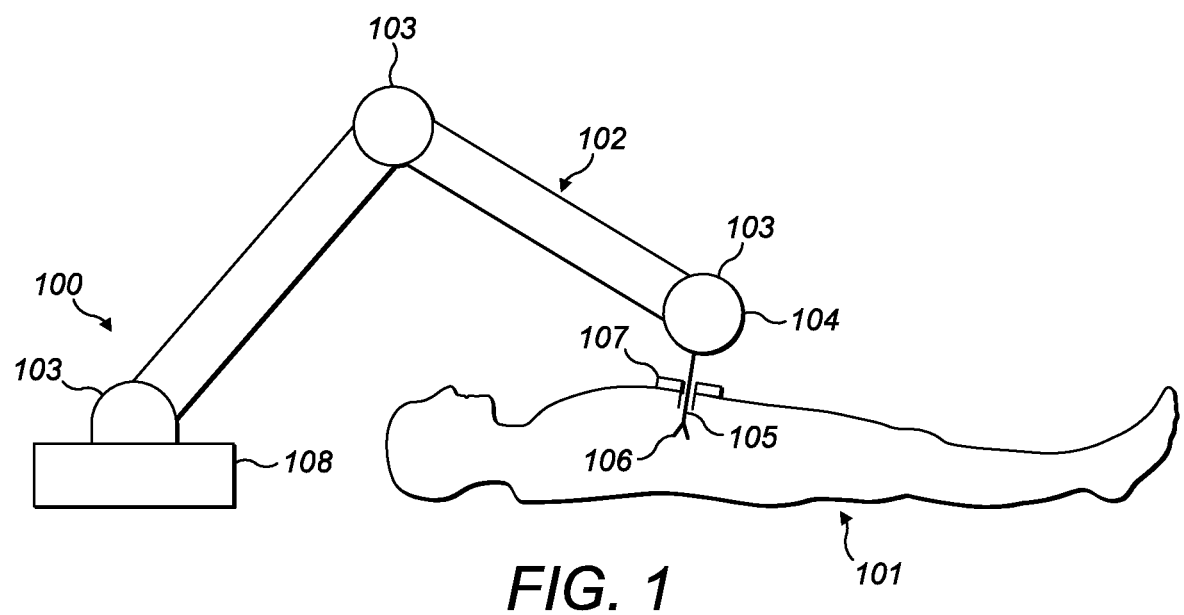
FIG. 1 illustrates a surgical robot performing a surgical procedure.
Figure 2:
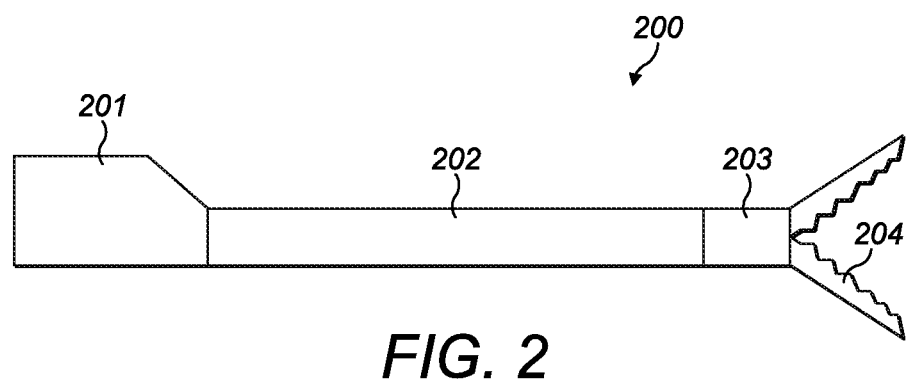
FIG. 2 illustrates a known surgical instrument.

The arm terminates in an attachment 305 for interfacing with the instrument 306. Suitably, the instrument 306 takes the form described with respect to FIG. 2. The attachment 305 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable to and detachable from the robot arm during the operation. Features of the drive assembly interface and the instrument interface aid their alignment when brought into engagement with each other, so as to reduce the accuracy with which they need to be aligned by the user.

The instrument 306 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to control unit 309. A control unit 309 comprises a processor 310 and a memory 311. Memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in memory 311 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

Figure 4:
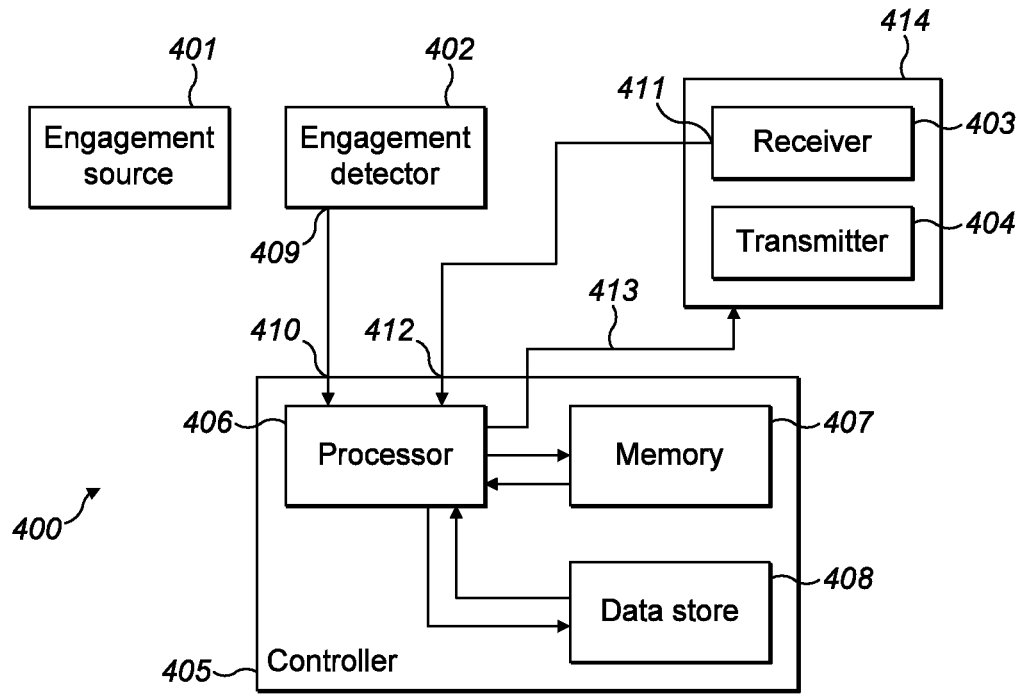
FIG. 4 illustrates schematically circuitry on the robot arm.
Figure 5:
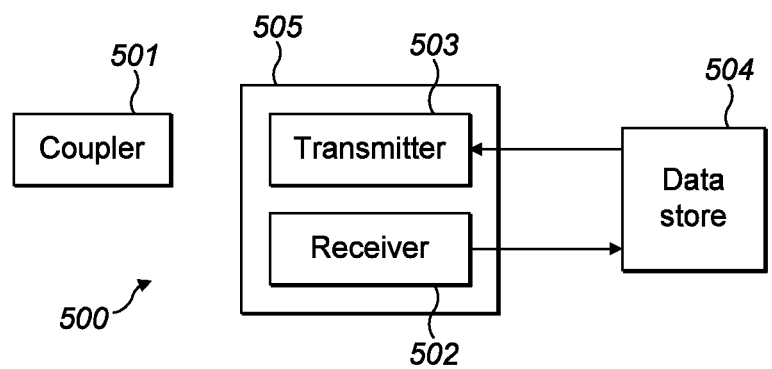
FIG. 5 illustrates schematically circuitry on the instrument.

FIG. 4 illustrates a schematic diagram of exemplary circuitry 400 on the robot arm 300 for detecting the instrument 306. FIG. 5 illustrates a schematic diagram of exemplary circuitry 500 on the instrument 306 for being detected by the robot arm 300.

Exemplary circuitry 400 comprises an engagement source 401 and an engagement detector 402. The engagement source 401 and engagement detector 402 may both be located on the robot arm interface. They are used by the robot arm to detect when the instrument 306 is engaged on the robot arm. Optionally, the robot arm may be capable of receiving communications from the instrument via receiver 403 and/or transmitting communications to the instrument via transmitter 404. The receiver 403 and/or transmitter 404 may both be located on the robot arm interface.

Circuitry 400 also depicts controller 405. Controller 405 comprises a processor 406, memory 407, and data store 408. Controller 405 may be one of the distributed controllers described above which is located on the robot arm, for example on or near the robot arm interface.

Alternatively, controller 405 may be the same as control unit 309, which may be located on or remote from the robot arm. The controller 405 receives an output 409 from the engagement detector 402 at input 410. The controller also receives an output 411 of the receiver 403 at input 412. Inputs 410 and 412 are both input to the processor 406. The processor outputs to and receives inputs from memory 407. The processor outputs to and receives inputs from data store 408. Memory 407 stores in a non-transient way software that is executable by the processor to control the operational mode of the robot arm in the manner described herein. The processor outputs a control signal 413 to the transmitter 404 and/or the receiver 403. The controller thereby controls the operation of the arm transmitter 404 and/or arm receiver 403 in dependence on the output of the engagement detector 402. Data store 408 may store parameter values of the instrument which the controller has derived from data received from arm receiver 403. Data store 408 may store an indication of whether the instrument is docked in the arm or not as determined from the output of the engagement detector 402. Data store 408 may be incorporated within memory 407. In this case, memory 407 is logically partitioned into a section for the data store 408 and a section for storing instructions for execution on processor 406. Data store 408 may be incorporated as registers in processor 406. Data store 408 may be one or more buffers.

Exemplary circuitry 500 comprises a coupler 501. The coupler 501 may be located on the instrument interface. Alternatively, as discussed further below, the coupler 501 may be located on either the robot arm interface or a surgical drape. In all of these examples, the coupler 501 is used to couple the engagement source 401 to the engagement detector 402, thereby enabling the robot arm to detect that the instrument 306 is engaged on the robot arm. Optionally, the instrument may be capable of receiving communications from the robot arm via receiver 502 and/or transmitting communications to the robot arm via transmitter 503. The receiver 502 and/or transmitter 503 may both be located on the instrument interface. Circuitry 500 also depicts data store 504. Data store 504 stores data indicative of the values of one or more parameters of the instrument 306. The data store 504 may store parameter values of the instrument. The data is retrieved from data store 504 to be transmitted by instrument transmitter 503. The receiver 502 outputs to data store 504, and the transmitter 503 receives an input from data store 504.

The engagement detector 402 is configured to only detect the engagement source 401 when the engagement source is coupled to the engagement detector by the coupler 501. When the coupler is not located so as to couple the engagement source to the engagement detector, the engagement detector does not detect the engagement source. The coupler 501 is located on the instrument interface, or the surgical drape or the robot arm interface in such a position that it only couples the engagement source 401 to the engagement detector 402 when the instrument interface is properly engaged with the robot arm interface. The instrument interface and robot arm interface are properly engaged when they are in alignment. The instrument interface and robot arm interface are properly engaged when the instrument interface elements and drive assembly interface elements are engaged and operable to transmit drive through from the robot arm to the instrument. Thus, if the instrument interface and robot arm interface are misaligned, the coupler will not couple the engagement source to the engagement detector. The coupler of a nearby instrument which is attached to a different robot arm will not couple the engagement source to the engagement detector.

In the examples in which the coupler 501 is either on the robot arm interface or on a surgical drape which shrouds the robot arm, the coupler may be located on a moveable feature. In the case that the coupler is on the robot arm interface, the moveable feature moves relative to the robot arm interface. When the instrument interface and the robot arm interface are not engaged, the moveable feature is located such that the coupler does not couple the engagement source 401 to the engagement detector 402. In the case that the coupler is on the drape, the moveable feature moves relative to the drape. When the drape has been applied to the robot arm (so as to provide a sterile barrier between the non-sterile robot arm and the sterile operating environment), the moveable feature is located proximal to the robot arm interface and moves relative to both the drape and the robot arm interface. When the instrument interface and the robot arm interface are not engaged (with the drape between them), the moveable feature is located such that the coupler does not couple the engagement source 401 to the engagement detector 402.

In these examples in which the coupler is on the robot arm interface or the drape, the instrument interface comprises a protrusion. The protrusion is located on the instrument interface such that when the instrument interface and robot arm interface are properly engaged, the protrusion pushes the moveable feature so as to cause the coupler to be located so as to couple the engagement source 401 to the engagement detector 402.

By incorporating the coupler onto the drape, this enables the controller 405 to determine that the drape has been correctly applied to the robot arm interface as well as that the instrument interface and robot arm interface have been correctly engaged. Only if all three components are correctly aligned and engaged will the engagement detector detect the engagement source.

The coupler 501 may couple the engagement source 401 to the engagement detector 402 by virtue of its proximity to the engagement source 401 and engagement detector 402. For example, the engagement source and/or the engagement detector may be short-range and spaced apart on the robot arm interface such that the engagement source is out of range of the engagement detector and hence the engagement detector does not detect the engagement source directly. When the instrument interface is engaged in the robot arm interface, the coupler is located sufficiently proximal to the instrument engagement source and instrument engagement detector that it is able to couple the engagement source to the engagement detector such that the engagement detector detects the engagement source. For example, this may be by connecting a circuit between the engagement source and the engagement detector.

In another example, the coupler 501 may couple the engagement source 401 to the engagement detector 402 by virtue of amplifying a property of the engagement source 401 to a level which the engagement detector 402 can detect. For example, the engagement detector may only be able to detect a property of the engagement source 401 above a threshold level. The level which the engagement detector 402 is exposed to in the absence of the coupler 501 is below the threshold level. When the instrument interface is engaged with the robot arm interface, the coupler amplifies the property sufficiently that the engagement detector 402 is exposed to a level of the property in excess of the threshold level, and hence the engagement detector detects the engagement source.

In another example, the coupler 501 may couple the engagement source 401 to the engagement detector 402 by virtue of re-directing an emission of the engagement source 401 to the engagement detector 402. The source emission may be directional, and directed away from the engagement detector 402 such that the engagement detector does not detect the engagement source directly. When the instrument interface is engaged in the robot arm interface, the source emission is directed towards the coupler 501. The coupler 501 is designed so as to re-direct the source emission such that it is directed towards the engagement detector 402, thereby enabling the engagement detector to detect the emission from the engagement source.

Suitably, instrument transmitter 503, instrument receiver 502, robot arm receiver 403, and robot arm transmitter 404 operate according to the same short-range wireless communications protocol. For example, they may operate according to an RFID (Radio Frequency Identification) protocol. In an exemplary implementation, they communicate according to a protocol that has a range of less than or the same as 4 cm. The protocol may have a range of less than or the same as 2 cm. The protocol may use NFC (Near Field Communication). Utilising a short-range wireless communications protocol as opposed to a wireless communications protocol that is not short-range reduces the likelihood of the instrument-arm communication interfering with other communication links in the operating theatre. It also reduces the likelihood of those other communication links interfering with the instrument-arm communication.

Figure 6:
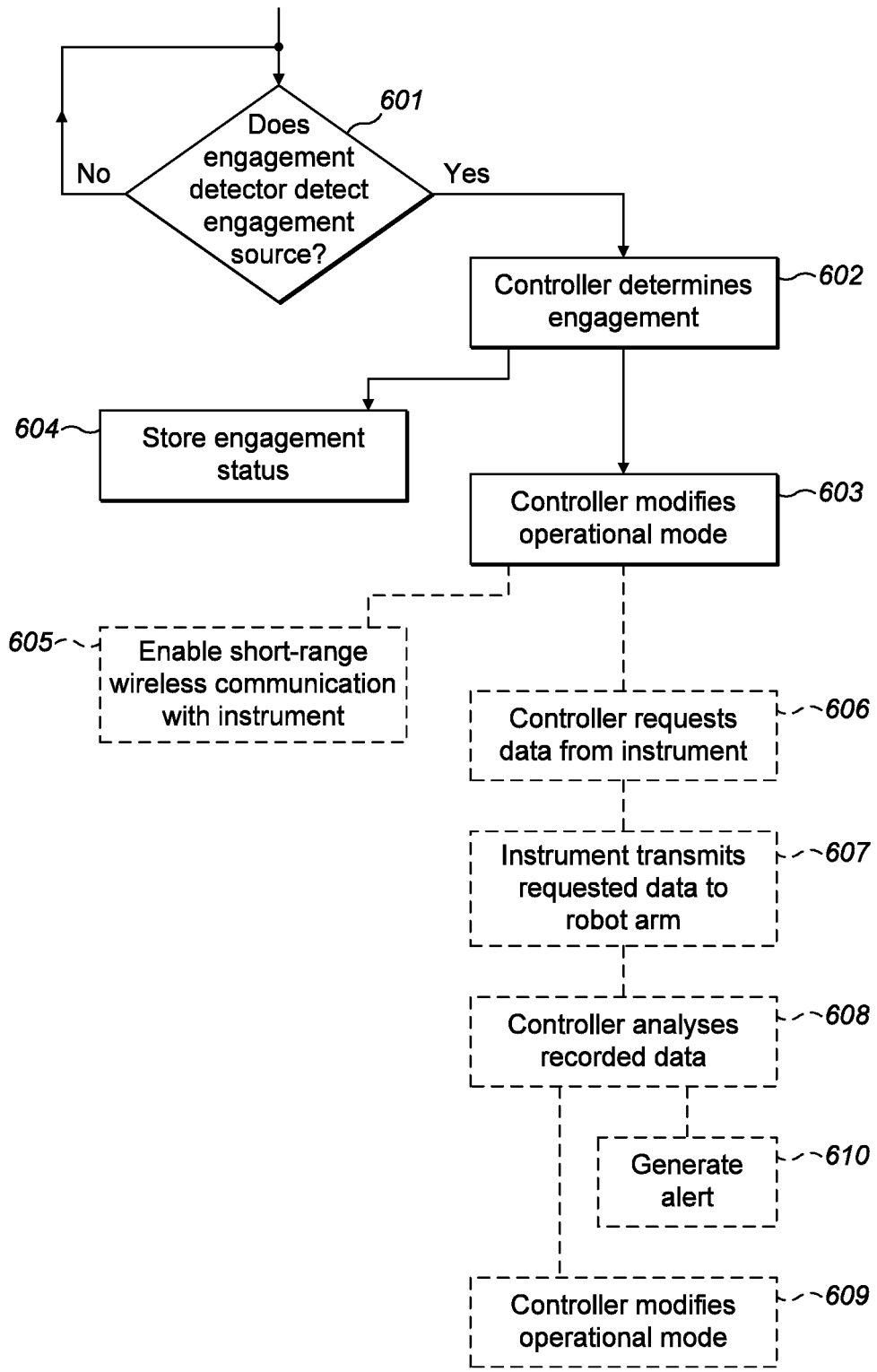
FIG. 6 is a flowchart illustrating a control method for detecting an instrument and responding to instrument detection.

FIG. 6 illustrates a method implemented by the circuitry of FIGS. 4 and 5. The engagement detector 402 outputs a signal to the controller 405. This signal is indicative of whether the engagement detector detects the engagement source. The engagement detector 402 may continually output a signal. In this case, the signal may have two states: a first state which indicates that the engagement detector is not currently detecting the engagement source, and a second state which indicates that the engagement detector is currently detecting the engagement source. Alternatively, the engagement detector 402 may only output a signal when it detects the engagement source. Alternatively, the engagement detector 402 may only output a signal when it does not detect the engagement source.

At step 601, the controller determines whether the engagement detector has detected the engagement source. If the answer is NO then the controller returns to step 601. A NO is indicated by a signal of the first state in the first example above. The processor may compare the received signal from the engagement detector to replica signals stored in the data store 408, and determine that the engagement detector has not detected the engagement source if the received signal matches a replica first state signal. A NO is indicated by the lack of a signal in the second example. A NO is indicated by the presence of a signal in the third example. If the answer is YES then the controller determines that the instrument interface is properly engaged in the robot arm interface at step 602. A YES is indicated by a signal of the second state in the first example above. The processor may compare the received signal from the engagement detector to replica signals stored in the data store 408, and determine that the engagement detector has detected the engagement source if the received signal matches a replica second state signal. A YES is indicated by the presence of a signal in the second example. A YES is indicated by the lack of a signal in the third example. At step 604, the controller may store an indication in the data store 408 that the instrument is docked in the robot arm.

At step 603, the controller responds to determining that the instrument interface is properly engaged in the robot arm interface by modifying an operational mode of the robot. For example, prior to step 601, the robot arm may have been in an operational mode in which no communication link is established between the robot arm 300 and the instrument 306. This may have been because the communication link had not yet been established. Alternatively, it may have been because the controller 405 had disabled the arm transmitter 404 and/or arm receiver 403 from communicating according to the short-range wireless communications protocol. In response to determining that the instrument interface is properly engaged in the robot arm interface, the controller may enable a short-range wireless communications link to be established between the arm receiver 403 or arm transceiver 414 and the instrument transmitter 503 or instrument transceiver 505. For example, the control signal may switch the receiving function of the arm receiver 403 on, thereby enabling it to receive data transmitted by the instrument transmitter 503. Alternatively, or additionally, the control signal may cause the arm transmitter 404 to request a connection with the instrument receiver 502. Following this, a short-range wireless communications link is established between the arm and the instrument.

At step 606, the controller 405 may control the arm transceiver 414 to transmit a query to the instrument. The arm transceiver 414 responds by transmitting the query to the instrument. The instrument receiver 502 receives the query. At step 607, the instrument responds to receipt of the query by retrieving the requested data from the data store 504, and transmitting the requested data from the instrument transmitter 503 to the robot arm. The arm receiver 403 receives the requested data and outputs it to the controller 405. That query may be a request for the instrument to provide data indicative of the value of one or more parameters of the instrument. These parameters include one, more or all of the following: instrument type, instrument identity, instrument usage data, and control data.

The instrument usage data may include one, more or all of the following: the number of times the instrument has been used, the number of uses of the instrument remaining before expiry, the total operation time of the instrument, the total operation time the instrument has left before expiry, the lifetime used, the lifetime remaining.

The control data may include parameters of the robot arm drive assembly that the instrument is to adopt. The control data may include parameters of the instrument that the robot arm is to adopt. For example, the control data may include one, more or all of the following: the functions of the drive assembly interface elements, the functions of the instrument interface elements, the range of travel of the drive assembly interface elements including the maximum and minimum travels, the range of travel of the instrument interface elements including the maximum and minimum travels, the neutral/rest position of the drive assembly interface elements, the neutral/rest position of the instrument interface elements, the range of travel of the instrument joints including the maximum and minimum travels, and the neutral/rest position of the instrument joints.

In one example, the data is a code. The code may be a number code. The value of one or more of the parameters of the instrument is embedded within the code. In other words, the value of the one or more parameters of the instrument are derivable from the code by analysing the code with an algorithm. In another example, the data itself includes the value of one or more of the parameters of the instrument. In either example, the data may be encrypted.

At step 608, the controller 405 extracts the requested parameter values from the received data. The derived parameter values are then stored in data store 408. The controller 405 decrypts the received data if it was encrypted. In the case that the received data is a code in which the parameter values are embedded, the controller inputs the code to an algorithm in order to determine the parameter values. The algorithm performs one or more functions on the code. Each function may determine one or more of the requested parameter values.

Optionally, at step 609, the controller 405 may modify an operational mode of the robot arm in response to the data it has received from the instrument. For example, the controller may change the operational mode of the robot arm by: engaging a manipulative mode of the instrument (in which the robot arm is operable to control manipulation of the end effector of the instrument), disengaging a manipulative mode of the instrument, engaging a manipulative mode which is specific to the instrument type identified in the data received from the instrument (i.e. specific to the instrument being a pair of grippers, a pair of scissors, a scalpel, etc), enabling a communication link with the instrument, disabling a communication link with the instrument, engaging a compliant mode of the robot arm (in which the robot arm responds to a manually applied external force to a limb/joint of the robot arm by controlling that limb/joint to move in the direction of the applied external force), engaging a non-compliant mode of the robot arm.

Optionally, at step 610, the controller 405 may generate an alert in response to the data it has received from the instrument. For example, an alert may be generated in response to one or more of the following: the instrument identity not matching an expected instrument identity, the instrument type not being compatible with the robot arm, and the instrument usage data indicating that the instrument does not have sufficient lifetime remaining to perform the operation.

It will be understood that the steps of the flowchart of FIG. 6 may be performed in a different order to that shown. Some steps may be omitted.

Figure 7:
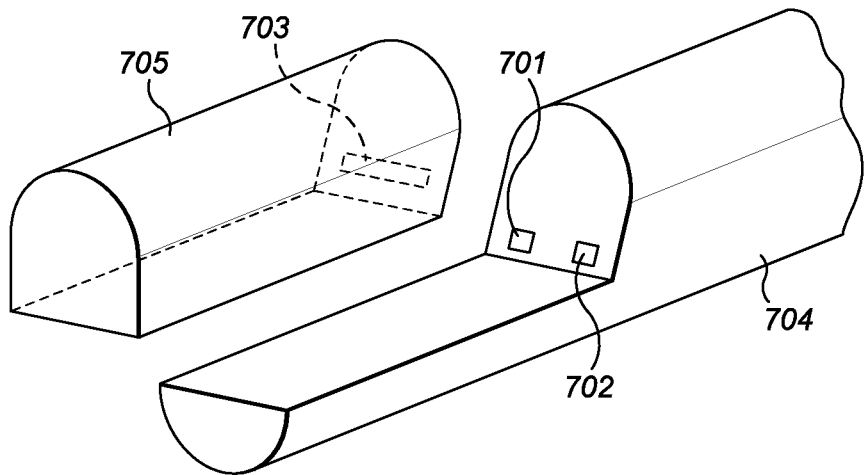
FIG. 7 illustrates a magnetic example of the circuitry of FIGS. 4 and 5.

FIG. 7 illustrates an example implementation of an engagement source, engagement detector and coupler arrangement. In this example, the engagement source 401 is a magnet or electromagnet 701. The engagement detector 402 is a sensor 702 which senses a magnetic field. For example, the engagement detector may be a Hall sensor. The coupler 703 is magnetically permeable. The coupler may have a high magnetic permeability. For example, the coupler may have a magnetic permeability $\mu \geq 1 \times 10^{-5}$ H/m. The coupler may have a magnetic permeability $\mu \geq 1 \times 10^{-3}$ H/m. In other words, the coupler is a susceptor material. The coupler may be composed of Mu metal.

The magnet 701 and sensor 702 are both located on the distal end of the robot arm. The magnet is spaced sufficiently apart from the sensor such that, in isolation and for the sensitivity of the sensor, the sensor 702 is unable to detect the magnet 701. The sensor 702 is only able to detect the magnet 701 when coupled to it by a further magnetically susceptible material external to the end of the robot arm. This further magnetically susceptible material is located sufficiently proximal to the magnet 701 and sensor 702 to enable the sensor 702 to detect the magnet 701. The coupler 703 may be located on the proximal end of the instrument 705. Alternatively, the coupler 703 may be located on a surgical drape or on the robot arm interface as described above. The locations of the magnet 701, the sensor 702 and the coupler 703 are such that, when the instrument interface is engaged to the robot arm interface, the coupler 703 is proximal to the magnet 701 and sensor 702. The magnetic flux of the magnet 701 is captured in the coupler 703. The coupler 703 thereby connects a circuit between the magnet 701 and the sensor 702. The sensor 702 thereby detects the magnet 701. The sensor 702 outputs an indication of this detection to the controller 405 as described with reference to FIG. 4.

Figure 8A:
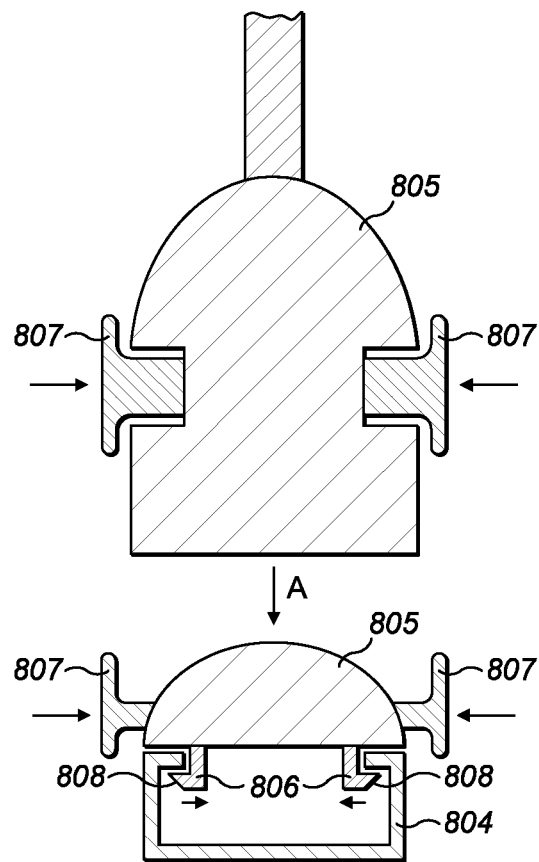
Figure 8B:
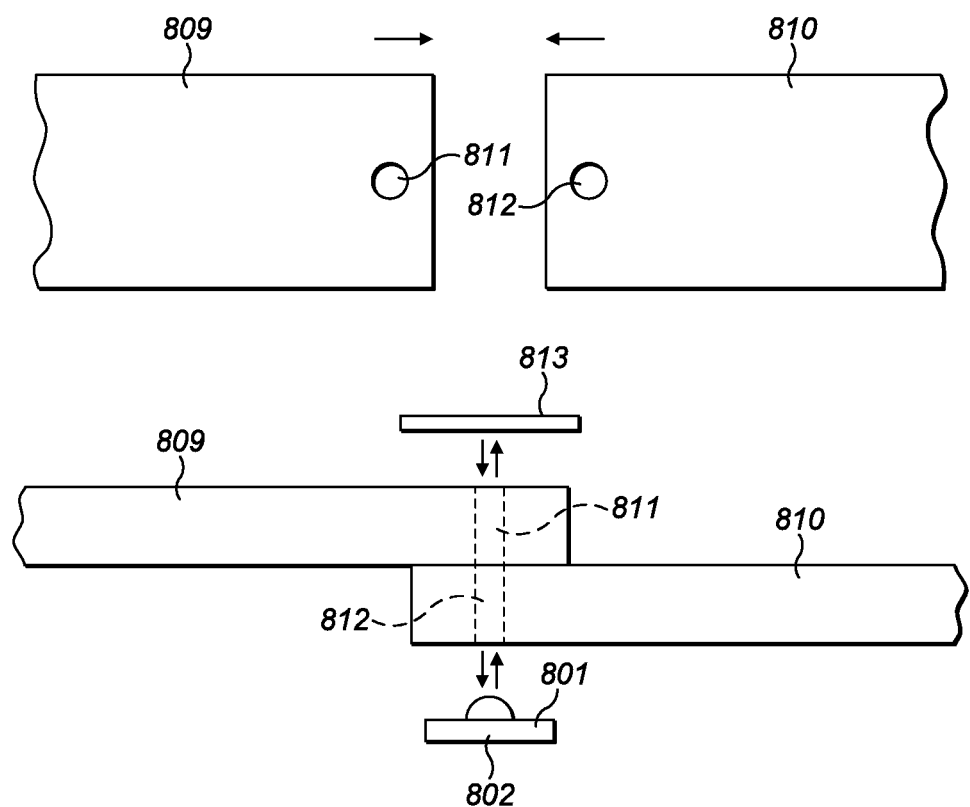

FIGS. 8A, 8B, and 8C illustrate further example implementations of an engagement source, engagement detector and coupler arrangement. In these examples, the engagement source is a light source 801 (such as an LED), and the engagement detector is a light sensor 802. The coupler provides a light path from the light source to the light sensor.

The light source 801 and light sensor 802 are both located on the distal end of the robot arm. FIG. 8B illustrates an example in which the light source and light sensor are in the same location on the robot arm. FIG. 8C illustrates an example in which the light source and light sensor are spaced apart on the robot arm. In both examples, the light from the light source 801 is directed away from the light sensor 802 such that, in isolation, the light sensor 802 is unable to detect the light from the light source 801. The light sensor 802 is only able to detect the light from the light source when that light is re-directed onto the light sensor by a coupler.

In the examples of FIGS. 8, when the instrument is disengaged from the robot arm, no light path is provided from the light source 801 to the light sensor 802. However, when the instrument interface is engaged with the robot arm interface, a light path is provided from the light source 801 to the light sensor 802. In both examples, the instrument interface comprises an engagement mechanism, shown in FIG. 8A, which is moveable between a disengaged configuration and an engaged configuration. In the disengaged configuration, no light path is provided between the light source and the light sensor. However, when the engagement mechanism is in the engaged configuration and when it is engaged with the robot arm, a light path is provided between the light source and the light sensor.

FIG. 8A illustrates two views of the instrument interface. The top figure illustrates a view from above the casing of the instrument interface 805. The bottom figure illustrates a cross-section through the instrument interface. The engagement mechanism comprises latches 806 which are connected to buttons 807. In the engaged configuration depicted in the bottom figure, the latches retain the instrument interface to the robot arm interface. To disengage the engagement mechanism, the buttons are depressed towards each other in the directions shown by the arrows. The buttons may be hand-operated. On depressing the buttons, the latches move towards each other. When the buttons are fully depressed, the engagement mechanism is in the disengaged configuration. This releases the instrument interface from the robot arm interface. The instrument interface may then be removed from the robot arm interface. When the buttons are released, the engagement mechanism returns to the engaged configuration.

The instrument interface may be engaged with the robot arm interface by depressing the buttons to move the engagement mechanism into the disengaged configuration as described above. The latches 806 may then be seated inside the robot arm interface. The buttons may then be released, causing the engagement mechanism to return to the engaged configuration. The instrument interface is thereby engaged in the robot arm interface.

The faces 808 of latches 806 which initially engage the robot arm interface may be angled as shown in FIG. 8A. With the instrument interface aligned and in contact with the robot arm interface, and the engagement mechanism in the engaged configuration, a force applied in direction A perpendicular to the direction in which the buttons depress, causes the latches to move into the engaged configuration with the robot arm interface. This action alone, i.e. without depressing the buttons 807, may be sufficient to move the engagement mechanism from an engaged configuration in which it is not engaged in the robot arm interface, to the engaged configuration in the robot arm interface shown in FIG. 8A. Alternatively, the instrument interface may be pushed in the direction A in combination with depressing the buttons 807 in order to move the engagement mechanism from an engaged configuration in which it is not engaged in the robot arm interface, to the engaged configuration in the robot arm interface shown in FIG. 8A.

FIGS. 8B and 8C both illustrate examples in which two portions of the engagement mechanism which move relative to each other when the engagement mechanism is actuated, each provide a barrier to light expect in one region in which they permit light to pass through them. When the engagement mechanism is in the disengaged configuration, the regions which permit light to pass through them in the two portions are not aligned, thus there is no light path through the engagement mechanism via these two portions. When the engagement mechanism is in the engaged configuration, the regions which permit light to pass through them in the two portions are aligned, thus there is a light path through the engagement mechanism via these two portions.

In the example of FIG. 8B, the two portions are plates 809, 810, each of which is connected to a different one of the buttons 807. Each plate comprises a hole 811, 812 which enables light to pass through it. The bottom figure of FIG. 8B illustrates the plates in the engaged configuration of the engagement mechanism. This view is perpendicular to the view in the top figure of FIG. 8B. In the engaged configuration, the plates 809, 810 overlap such that the holes 811, 812 align. Thus, a light path is provided through the plates 809, 810. The instrument interface comprises a reflector 813 which reflects light. The reflector 813 is positioned and orientated such that light which passes through the aligned holes 811, 812 towards the reflector, is then reflected back through the holes 811, 812 by the reflector. When the instrument interface is properly engaged in the robot arm interface with the engagement mechanism in the engaged configuration, the light source 801 is located relative to the plates 809, 810 such that the light emitted from the light source 801 is directed through the holes 811, 812 to the reflector 813, and the light sensor 802 is located relative to the plates 809, 810 such that the light reflected from the reflector 813 and directed through the holes 811, 812 is sensed by the light sensor 802. When the instrument interface and robot arm interface are not properly engaged, the light source 801, light sensor 802, holes 811 and 812 and reflector 813 are not all aligned. Thus, light emitted from the light source 801 is not detected by the light sensor 802. The sensor 802 outputs an indication of the detected light and hence the detected engagement to the controller 405 as described with reference to FIG. 4.

In the example of FIG. 8C, the two portions are plates 814, 815, each of which is connected to a different one of the buttons 807. Each plate comprises two holes 816a, 816b, 817a, 817b which enable light to pass through them. The bottom figure of FIG. 8C illustrates the plates in the engaged configuration of the engagement mechanism. This view is perpendicular to the view in the top figure of FIG. 8c. The figure on the right of FIG. 8C also illustrates the plates in the engaged configuration of the engagement mechanism. This view is perpendicular to the view in the top figure of FIG. 8C, and also perpendicular to the view in the bottom figure of FIG. 8C. In the engaged configuration, the plates 814, 815 overlap such that the holes 816a, 817a align and the holes 816b, 817b align. Thus, two light paths are provided through the plates 814, 815. The instrument interface comprises a prism 818 which redirects light. The prism 818 is positioned and orientated such that light which passes through the aligned holes 817b, 816b towards the prism, is redirected by the prism through the aligned holes 816a, 817a. When the instrument interface is properly engaged in the robot arm interface with the engagement mechanism in the engaged configuration, the light source 801 is located relative to the plates 814, 815 such that the light emitted from the light source 801 is directed through the holes 817b, 816b to the prism 818, and the light sensor 802 is located relative to the plates 814, 815 such that the light redirected by the prism 818 and directed through the holes 816a, 817a is sensed by the light sensor 802. When the instrument interface and robot arm interface are not properly engaged, the light source 801, the holes 817b, 816b, and the prism 818 are not all aligned and/or the light sensor 802, the holes 816a, 817a, and the prism 818 are not all aligned. Thus, light emitted from the light source 801 is not detected by the light sensor 802. The sensor 802 outputs an indication of the detected light and hence the detected engagement to the controller 405 as described with reference to FIG. 4.

Although FIG. 8B illustrates one pair of aligned holes, and FIG. 8C illustrates two pairs of aligned holes, it will be appreciated that any number of aligned holes in combination with any number of reflectors, prisms and/or light pipes may be used to provide a light path from the robot arm interface through the instrument interface and back to the robot arm interface.

Figure 9:
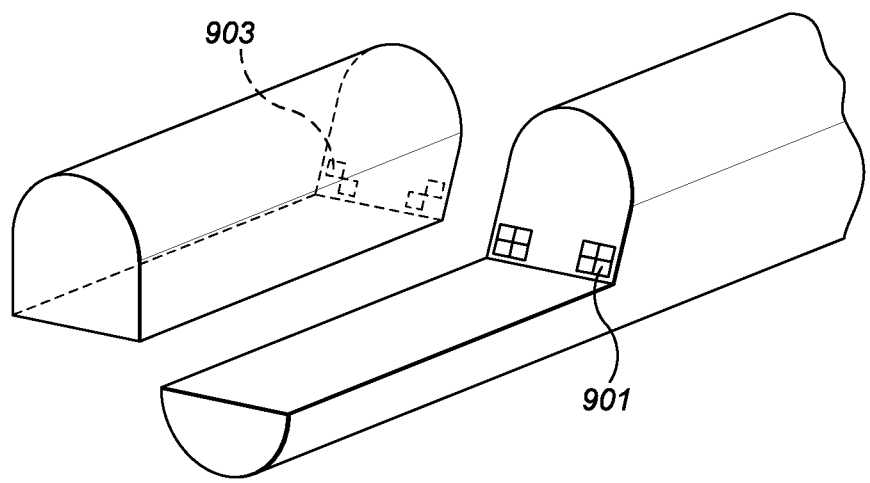
FIG. 9 illustrates a sensor array example of the circuitry of FIGS. 4 and 5.

FIG. 9 illustrates a further example implementation of an engagement source, engagement detector and coupler arrangement. In this example, the engagement source 401 and the engagement detector 402 are a sensor array 902. For example, the sensor array 902 may be a capacitive sensor array or an inductive sensor array. The coupler 903 is a metal array.

The engagement source and the engagement detector are the same component, i.e. the same sensor array on the robot arm interface. The sensor array is activated by the metal array coupler when that metal array coupler is sufficiently proximal to the sensor array. The metal array coupler may be on the instrument interface, on the surgical drape or on the robot arm interface. The metal array coupler is sufficiently proximal to the sensor array to activate the sensor array when the instrument interface and robot arm interface are engaged. If the instrument interface and robot arm interface are not properly engaged, then the metal array coupler is not sufficiently proximal to the sensor array on the robot arm interface to activate the sensor array.

In the example in which the sensor array is a capacitive sensor array, the electric field modified by the metal array is detected by the capacitive sensor array. In the example in which the sensor array is an inductive sensor array, the inductive sensor array may comprise inductor coils. The magnetic field modified by the metal array is detected by the inductive sensor array. In either example, the sensor array 901 may only be activated by contact with the metal array 903. This contact may only be achieved when the instrument interface and robot arm interface are properly engaged. The sensor 901 outputs an indication of the detection of the metal array to the controller 405 as described with reference to FIG. 4.

The sensor array 901 may be configured to only generate a signal indicative that the instrument interface and robot arm interface are engaged if a predetermined pattern of the sensors of the sensor array are activated. If sensors additional to the predetermined pattern of sensors are activated, then the signal indicative of instrument engagement is not activated. This increases the robustness and reliability of the instrument detection mechanism by reducing the likelihood of the sensor array being activated by something other than the metal array. For example, an operator's hand or even dust or moisture may activate sensors of the sensor array 901. However, these are unlikely to activate only the predetermined pattern of sensors.

The metal pads of the coupler 903 may be arranged so as to activate some but not all of the sensors of the sensor array 901. The activated sensors are in the predetermined pattern when the instrument interface is engaged with the robot arm interface. The activated sensors are not in the predetermined pattern when the instrument interface is not properly engaged with the robot arm, for example if it is partially attached or misaligned.

FIGS. 10A-F illustrate some example sensor arrays and corresponding metal arrays. The metal array has a pattern which matches the predetermined pattern described above. In each case, only when the instrument interface and robot arm interface are properly engaged, are the metal array and sensor array aligned so as to cause the metal array to activate the predetermined pattern of sensors of the sensor array.

Figure 10A:
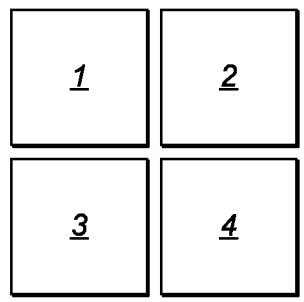
FIGS. 10A, 10B, 10C, 10D, 10E and 10F illustrates arrangements of the sensor array and metal array of FIG. 9.
Figure 10B:
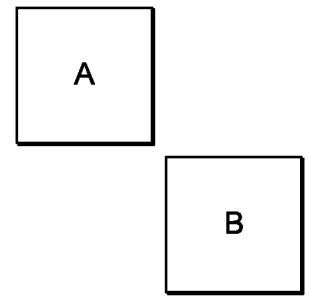

FIG. 10A illustrates a sensor array 901 having four sensors, and FIG. 10B illustrates a corresponding metal array 903 having two metal pads. The metal pads and sensors are each the same shape and size. Metal pads A and B are located such that they activate sensors 1 and 4 respectively when the instrument interface and robot arm interface are properly engaged. Sensors 2 and 3 are not activated by the metal array when the instrument interface and robot arm interface are properly engaged.

Figure 10C:
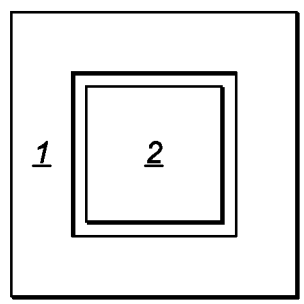
Figure 10D:
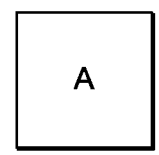

FIG. 10C illustrates a sensor array 901 having two sensors, and FIG. 10D illustrates a corresponding metal array 903 having one metal pad. The metal pad A is the same size and shape as sensor 2. The metal pad A is located such that it activates sensor 2 when the instrument interface and robot arm interface are properly engaged. Sensor 1 is not activated by the metal array when the instrument interface and robot arm interface are properly engaged.

Figure 10E:
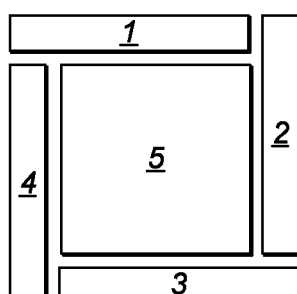
Figure 10F:
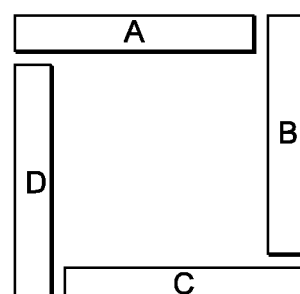

FIG. 10E illustrates a sensor array 901 having five sensors, and FIG. 10F illustrates a corresponding metal array 903 having four metal pads. Metal pad A matches the shape and size of sensor 1, metal pad B matches the shape and size of sensor 2, metal pad C matches the shape and size of sensor 3, and metal pad D matches the shape and size of sensor 4. Metal pads A, B, C and D are located such that they activate sensors 1, 2, 3 and 4 respectively when the instrument interface and robot arm interface are properly engaged. Sensor 5 is not activated by the metal array when the instrument interface and robot arm interface are properly engaged.

The sensor array may have a plurality of predetermined patterns of activated sensors, in response to which it is configured to generate a signal indicative that the instrument interface and robot arm interface are engaged. Each predetermined pattern may indicate a parameter of the instrument, such as the instrument identity or instrument type of the instrument. The engagement detector may be configured to output an indication of this instrument parameter to the controller 405 in addition to or instead of the engagement indication described with reference to FIG. 4.

For example, the sensor array of FIG. 10A may have three predetermined patterns: (i) activation of sensor 1 only, (ii) activation of sensor 4 only, and (iii) activation of sensors 1 and 4. Correspondingly, the instrument coupler 903 may be a metal array having metal pad A only, metal pad B only, or metal pads A and B. It will be appreciated that the sensor array may be provided with further discrete sensors than those shown in FIG. 10 so as to detect further predetermined patterns.

The robot arm transceiver 414 may comprise an RFID antenna coil. The instrument transceiver 505 may comprise an RFID tag. The RFID antenna coil interrogates the RFID tag, in response to which the RFID tag provides the instrument's identity to the robot arm. In the example that the sensor array is an inductive sensor array, the RFID antenna coil may be the inductive sensor array. Similarly, the RFID tag may be the metal array coupler.

The main components of the instrument engagement detection mechanisms described herein are located on the robot arm interface not the instrument interface. The instrument is a consumable which is utilised until its expiry and then disposed of. The lifetime of instruments are generally a few operations. Thus, the examples described herein locate the majority of the components and hence the cost of the instrument engagement detection mechanism on the robot arm rather than the instrument.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical robot comprising:
a robot arm base connected to a distal robot arm link via a series of intermediate articulated robot arm links;
a robot arm interface attached to the distal robot arm link, the robot arm interface configured to engage an instrument interface of a surgical instrument, the robot arm interface comprising:
an instrument engagement source; and
an instrument engagement detector spaced apart from the instrument engagement source such that the instrument engagement source is out of range of the instrument engagement detector, and configured to only detect the instrument engagement source when the instrument engagement source is coupled to the instrument engagement detector by a coupler; and
a controller configured to determine that an instrument interface of a surgical instrument is engaged with the robot arm interface in response to the instrument engagement detector detecting the instrument engagement source.

2. The surgical robot as claimed in claim 1, wherein the instrument engagement detector is configured to only detect the instrument engagement source via the coupler when the instrument interface and the robot arm interface are engaged.

3. The surgical robot as claimed in claim 1, wherein the instrument engagement source and instrument engagement detector are short-range and only coupleable by a coupler located proximally to both the instrument engagement source and the instrument engagement detector.

4. The surgical robot as claimed in claim 1, wherein the controller is configured to modify an operational mode of the surgical robot in response to the instrument engagement detector detecting the instrument engagement source.

5. The surgical robot as claimed in claim 1, further comprising a receiver configured to receive data from the surgical instrument over a short-range wireless communications link with the surgical instrument, wherein the controller is configured to respond to the instrument engagement detector detecting the instrument engagement source by enabling the short-range wireless communications link between the receiver and a transmitter of the surgical instrument to be established.

6. The surgical robot as claimed in claim 5, further comprising a transmitter configured to transmit data to the surgical instrument over the short-range wireless communications link, wherein the controller is configured to respond to the instrument engagement detector detecting the instrument engagement source by transmitting a request for data from the transmitter to the surgical instrument.

7. The surgical robot as claimed in claim 5, further comprising a surgical instrument comprising an instrument interface, wherein the instrument interface comprises an instrument transmitter configured to transmit data over the short-range wireless communications link.

8. The surgical robot as claimed in claim 1, wherein the instrument engagement source is a magnet, and the instrument engagement detector is a Hall sensor.

9. The surgical robot as claimed in claim 8, wherein the magnet is spaced apart from the Hall sensor on the robot arm interface such that the magnet is only detectable by the Hall sensor when coupled to the Hall sensor by a magnetically permeable coupler located proximal to the magnet and Hall sensor.

10. The surgical robot as claimed in claim 1, wherein the instrument engagement source is a light source, and the instrument engagement detector is a light sensor.

11. The surgical robot as claimed in claim 10, wherein light from the light source is directed away from the light sensor such that light from the light source is only detectable by the light sensor when directed onto the light sensor by a coupler which provides a light path from the light source to the light sensor.

12. The surgical robot as claimed in claim 10, further comprising a surgical instrument comprising an instrument interface, wherein the instrument interface comprises an engagement mechanism moveable between a disengaged configuration and an engaged configuration, and wherein the coupler provides a light path from the light source to the light sensor when the instrument interface and robot arm interface are engaged and the engagement mechanism is in the engaged configuration.

13. The surgical robot as claimed in claim 12, wherein the coupler comprises a series of openings on the engagement mechanism, the openings configured to align to form the light path only when the mechanism is in the engaged configuration.

14. The surgical robot as claimed in claim 1, wherein the instrument engagement source and the instrument engagement detector are collectively a sensor array which is configured to be activated by a metal array coupler located proximal to the sensor array.

15. The surgical robot as claimed in claim 14, wherein the sensor array comprises a plurality of sensors, and the sensor array is configured to be activated when a predetermined pattern of the plurality of sensors is activated.

16. The surgical robot as claimed in claim 15, wherein the controller is configured to identify the surgical instrument from the activated predetermined pattern of the plurality of sensors.

17. The surgical robot as claimed in claim 1, wherein the robot arm interface comprises the coupler.

18. The surgical robot as claimed in claim 1, further comprising a surgical instrument comprising an instrument interface, and wherein the instrument interface comprises the coupler.

19. The surgical robot as claimed in claim 1, further comprising a surgical instrument comprising an instrument interface, and a surgical drape for draping the robot arm, the drape comprising the coupler.

20. The surgical robot as claimed in claim 1, wherein the coupler is configured to connect a circuit between the instrument engagement source and the instrument engagement detector.

* * * * *